(12) United States Patent
Su et al.

(10) Patent No.: US 9,036,883 B2
(45) Date of Patent: May 19, 2015

(54) SYSTEM AND METHODS FOR DETECTING LIVER DISEASE

(75) Inventors: Grace L. Su, Ann Arbor, MI (US); Stewart Wang, Ann Arbor, MI (US); Hannu Huhdanpaa, Edina, MN (US)

(73) Assignee: The Regents of The University of Michigan, Ann Arbor, MI (US)

( * ) Notice: Subject to any disclaimer, the term of this patent is extended or adjusted under 35 U.S.C. 154(b) by 605 days.

(21) Appl. No.: 13/346,387

(22) Filed: Jan. 9, 2012

(65) Prior Publication Data

US 2012/0177260 A1    Jul. 12, 2012

Related U.S. Application Data

(60) Provisional application No. 61/431,197, filed on Jan. 10, 2011.

(51) Int. Cl.
*G06K 9/00* (2006.01)
*G06T 7/00* (2006.01)
*G06T 7/60* (2006.01)
*A61B 6/00* (2006.01)
*A61B 5/00* (2006.01)

(52) U.S. Cl.
CPC .............. *G06T 7/0012* (2013.01); *A61B 5/4244* (2013.01); *G06T 7/602* (2013.01); *G06T 2207/10081* (2013.01); *G06T 2207/20076* (2013.01); *G06T 2207/30056* (2013.01); *A61B 6/5217* (2013.01); *Y10S 128/922* (2013.01)

(58) Field of Classification Search
None
See application file for complete search history.

(56) References Cited

U.S. PATENT DOCUMENTS

| | | | |
|---|---|---|---|
| 5,776,063 A * | 7/1998 | Dittrich et al. | 600/408 |
| 7,236,619 B2 | 6/2007 | Doi et al. | |
| 7,333,845 B2 | 2/2008 | Hundley et al. | |
| 7,346,209 B2 | 3/2008 | Gokturk et al. | |
| 7,359,538 B2 | 4/2008 | Zeng et al. | |
| 7,545,979 B2 | 6/2009 | Fidrich et al. | |
| 7,643,663 B2 | 1/2010 | Wiemker et al. | |
| 7,828,735 B2 | 11/2010 | Holmes et al. | |
| 7,840,247 B2 | 11/2010 | Liew et al. | |
| 2004/0101086 A1 * | 5/2004 | Sabol et al. | 378/4 |
| 2005/0112691 A1 * | 5/2005 | Callewaert et al. | 435/7.1 |
| 2005/0215883 A1 | 9/2005 | Hundley et al. | |
| 2006/0014294 A1 * | 1/2006 | Contreras et al. | 436/86 |

(Continued)

OTHER PUBLICATIONS

Aguirre et al. "Liver Fibrosis: Noninvasive Diagnosis with Double Contrast Material—enhanced MR Imaging", May 2006, Radiology: vol. 239: No. 2, pp. 425-437.*

(Continued)

*Primary Examiner* — Matthew Bella
*Assistant Examiner* — Jason Heidemann
(74) *Attorney, Agent, or Firm* — Harness, Dickey & Pierce, P.L.C.

(57) ABSTRACT

A noninvasive, quantitative imaging technique is presented for detecting and diagnosing liver disease, such as cirrhosis. The technique includes: capturing scan data from a subject using computed tomography or another type of imaging method and extracting image data representing the liver from the scan data. Various measures of the liver may be obtained from image data and then used to compute random variables of a statistical model, where the model is predictive of a medical condition of the liver and comprised of random variables that are indicative of at least one of a shape or texture of the liver. Output from the statistical model provides an indication of an undesirable condition of the liver.

22 Claims, 4 Drawing Sheets

(56) References Cited

U.S. PATENT DOCUMENTS

| | | | |
|---|---|---|---|
| 2006/0216238 A1 | 9/2006 | Manchester et al. | |
| 2007/0008317 A1* | 1/2007 | Lundstrom | 345/424 |
| 2007/0156047 A1 | 7/2007 | Nagler et al. | |
| 2007/0189590 A1 | 8/2007 | Fidrich et al. | |
| 2007/0242865 A1* | 10/2007 | Fenchel et al. | 382/128 |
| 2008/0063136 A1* | 3/2008 | Ohyu et al. | 378/4 |
| 2008/0107317 A1* | 5/2008 | Jeong et al. | 382/131 |
| 2008/0119718 A1 | 5/2008 | Hundley et al. | |
| 2008/0123927 A1* | 5/2008 | Miga et al. | 382/131 |
| 2008/0240527 A1* | 10/2008 | Keller | 382/128 |
| 2008/0305046 A1 | 12/2008 | Hafezi-Moghadam | |
| 2008/0311036 A1 | 12/2008 | Wang et al. | |
| 2009/0262993 A1* | 10/2009 | Kotsianti et al. | 382/128 |
| 2010/0080757 A1 | 4/2010 | Haaga et al. | |
| 2010/0094118 A1 | 4/2010 | Kobayashi et al. | |
| 2010/0142775 A1 | 6/2010 | Ganeshan et al. | |
| 2011/0188706 A1* | 8/2011 | Zhou | 382/103 |
| 2011/0313276 A1* | 12/2011 | Cales et al. | 600/410 |
| 2012/0010824 A1* | 1/2012 | Cales | 702/21 |
| 2012/0058916 A1* | 3/2012 | Glezer et al. | 506/9 |
| 2012/0207268 A1* | 8/2012 | Qian et al. | 378/4 |
| 2012/0230572 A1* | 9/2012 | Kohlberger et al. | 382/131 |

OTHER PUBLICATIONS

Jirak et al. "Texture Analysis of Human Liver," 2002, Journal Of Magnetic Resonance Imaging, vol. 15, pp. 68-74.*

Szczypinski et al. "MaZda—a Software for Texture Analysis", 2007, IEEE: International Symposium on Information Technology Convergence, pp. 245-249.*

D. Rockey, "Noninvasive Assessment of Liver Fibrosis and Portal Hypertension With Transient Elastography", Gastroenterology 2008.

K. Ito, et al., "Imaging Diagnosis of Cirrhosis and Chronic Hepatitis", Intervirology 2004.

W. Torres, et al., "Computed Tomography of Hepatic Morphologic Changes in Cirrhosis of the Liver", Journal of Computer Assisted Tomography 1986.

A. Keedy, et al., "Diagnosis of Cirrhosis by Spiral Computed Tomography: A Case-Control Study With Feature Analysis and Assessment of Interobserver Agreement", Journal of Computer Assisted Tomography 2008.

* cited by examiner

SYSTEM AND METHODS FOR DETECTING LIVER DISEASE

CROSS-REFERENCE TO RELATED APPLICATIONS

This application claims the benefit of U.S. Provisional Application No. 61/431,197, filed on Jan. 10, 2011. The entire disclosure of the above application is incorporated herein by reference.

FIELD

The present disclosure relates to noninvasive and quantitative imaging techniques for detecting and diagnosing liver disease.

BACKGROUND

The development of cirrhosis is the end consequence of all chronic liver disease and represents an important clinical landmark. With development of cirrhosis, one can anticipate decompensation accompanied by esophageal varices, ascites and hepatic encephalopathy and an increased incidence of hepatocellular carcinoma. All these factors determine treatment guidelines including the conditions for screening, vaccination, and liver transplantation referral. It also impacts clinical decision making including surgical risk assessments and medication choices. Thus, making the diagnosis is paramount. At the present time, a liver biopsy is the gold standard. However, it entails a small but significant risk of morbidity and mortality. Pain is the most common complaint and has been reported to be as high as 84%. Bleeding is estimated to occur in 0.1 to 2% and death has been reported to occur in approximately 0.1% of cases. In addition to these inherent risks, there is also concern for sampling error since each biopsy represents only 1/50,000 of the liver and geographic distribution of cirrhosis is not uniform. Further compounding the problem is a 10-20% intra-observer discrepancy among pathologists. These limitations have prompted significant efforts in developing noninvasive techniques for the detection of fibrosis and cirrhosis.

Therefore, it is desirable to develop noninvasive techniques for detecting and diagnosing liver disease, including cirrhosis. This section provides background information related to the present disclosure which is not necessarily prior art.

SUMMARY

A computer-implemented method is presented for detecting an undesirable medical condition of a liver in a subject. The method includes: receiving image data representing a liver of a subject; determining a measure of the liver from the image data; determining a random variable from the measure of the liver, where the random variable is indicative of at least one of a shape or texture of the liver; and detecting an undesirable condition of the liver using a statistical model comprised of the random variable.

In another aspect of this disclosure, a computer-implemented system is presented for detecting an undesirable medical condition of a liver in a subject. The system is comprised generally of an imaging device and a computing device. The imaging device is configured to capture image data of the subject using, for example, computed tomography. The computing device includes an image processor and a data analyzer. The image processor is configured to receive image data from the imaging device and extract a subset of the image data, where the subset of image data includes the liver of the subjects. The data analyzer operates to determine a measure of the liver from the subset of image data and compute the random variables of a statistical model, where the statistical model is predictive of a medical condition of a liver.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

Figure 1:
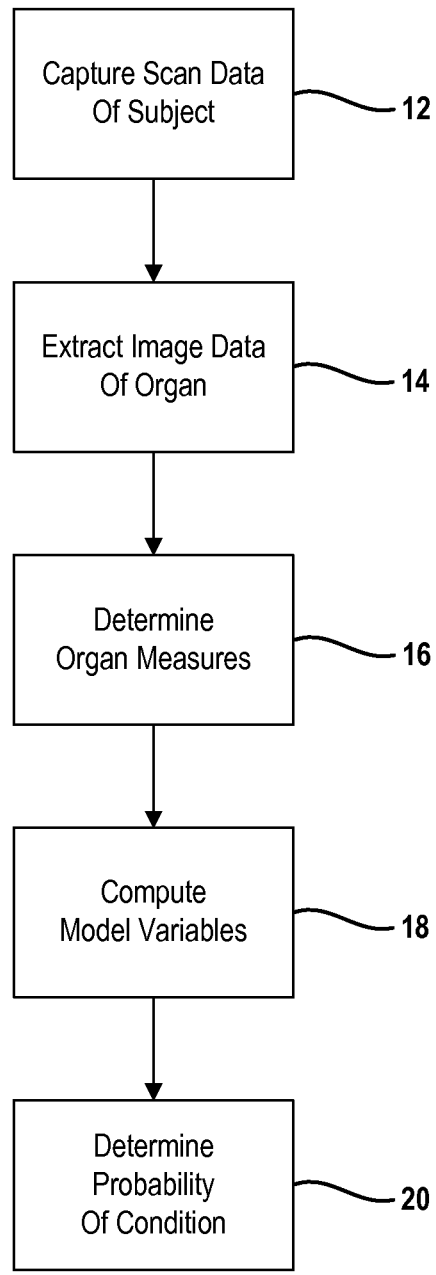
FIG. 1 is a diagram providing an overview of a quantitative method for detecting and diagnosing liver disease.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 provides an overview of a quantitative method for detecting and diagnosing liver disease, such as cirrhosis, in a subject. The detection scheme relies upon quantitative image analysis of the liver in the subject. Thus, image data for an abdominal area of the subject is first captured as indicated at 12. In an exemplary embodiment, the image data is further defined as stacks of two-dimensional images using computed tomography. Image data for the subject may also be captured using other types of imaging techniques, such as magnetic resonance imaging or ultrasonic imaging. Such image data made be two-dimensional or three-dimensional and is referred to herein generally as scan data. While reference is made throughout this disclosure to livers, it is readily understood that the quantitative methods set forth below are also extendable to other types of organs.

Next, image data representing the liver is extracted at 14 from the scan data using image processing software. In an exemplary embodiment, the image data for the liver is extracted using a three-dimensional surface model of the liver. That is, the surface model of the liver is first constructed from the scan data and may be stored, for example, as a stereo-lithography mesh (STL) file. The scan data, along with the surface model, is then loaded into an image processing tool, such as the MATLAB® software. The surface model is used to limit the scan data to points on or within the surface of the liver, thereby resulting in a stack of two-dimensional data slices representing the liver. Other techniques for constructing the image data are also contemplated by this disclosure.

Various measures or parameters related to the liver may be determined automatically at 16 from the image data. For example, a volume and/or a surface area for the entire liver may be computed from the image data. In other examples, measures may be computed from one or more slices of image data, such as a perimeter and/or an area of a given data slice. In an exemplary embodiment, the slice of data having the left tip of the liver is preferably determined from the stack of data slices. Selecting a particular slice enables comparison of metrics across subjects. Measures may be computed from a single data slice or as an average over a grouping of data slices adjacent (e.g., two slices above and below) the selected slice.

In yet other examples, measures may pertain to a bounding box which encases the liver, where a bounding box is understood to be the smallest possible 3-dimensional rectangular box that contains the liver. In the exemplary embodiment, the bounding box is aligned with the 3 axes of the CT scan, which are called the X, Y, and Z axes here. In terms of the human body orientation, X-axis is the lateral-medial axis, Y-axis is the anterior-posterior axis, and the Z-axis is the craniocaudal axis. The bounding box volume is the product of the liver extents in each of these three dimensions. Dimensions of the bounding box may be used to derive variables indicative of the shape of the liver as further described below. Moreover, other types of measures related to the liver are contemplated and thus fall within the broader aspects of this disclosure.

Predictive statistical models were developed to evaluate the various measures of the liver and quantitatively detect an undesirable medical condition of the liver, such as cirrhosis. In this example, changes in the shape or texture of the liver are known to be indicators of cirrhosis. Therefore, the statistical models are comprised of one or more random variables, where the random variables are indicative of shape or texture of the liver. Depending upon the type of medical condition being detected, the random variables may correlate to other attributes of the organ. Exemplary random variable may include but are not limited to a ratio between two dimension of the bounding box, a ratio between a volume of the liver and a volume of the bounding box, a ratio between a perimeter of a given data slice and an area of a given data slice, a ratio between a perimeter of a given data slice and a body surface area for the subject, a ratio between an area of the given data slice and the body surface area for the subject, a ratio between a volume of the liver and the body surface area for the subject, a ratio between a surface area of the liver and the body surface area for the subject and the like. Additionally, the model may also include other variables pertaining to the subject, such as age, gender, height, weight, blood characteristics, etc. In an exemplary embodiment, the statistical model is further defined as a logistic regression model although other types of statistical models are contemplated by this disclosure. Methods for developing statistical models from training data are readily known in the art.

To detect or diagnose the liver condition, the image data for a given subject is evaluated in relation to the statistical model. Specifically, random variable(s) for the model are determined at 17 from the image data and a probability of the liver condition is computed at 18 using the model. In this way, the liver condition is determined quantitatively from the image data of subject.

Figure 2:
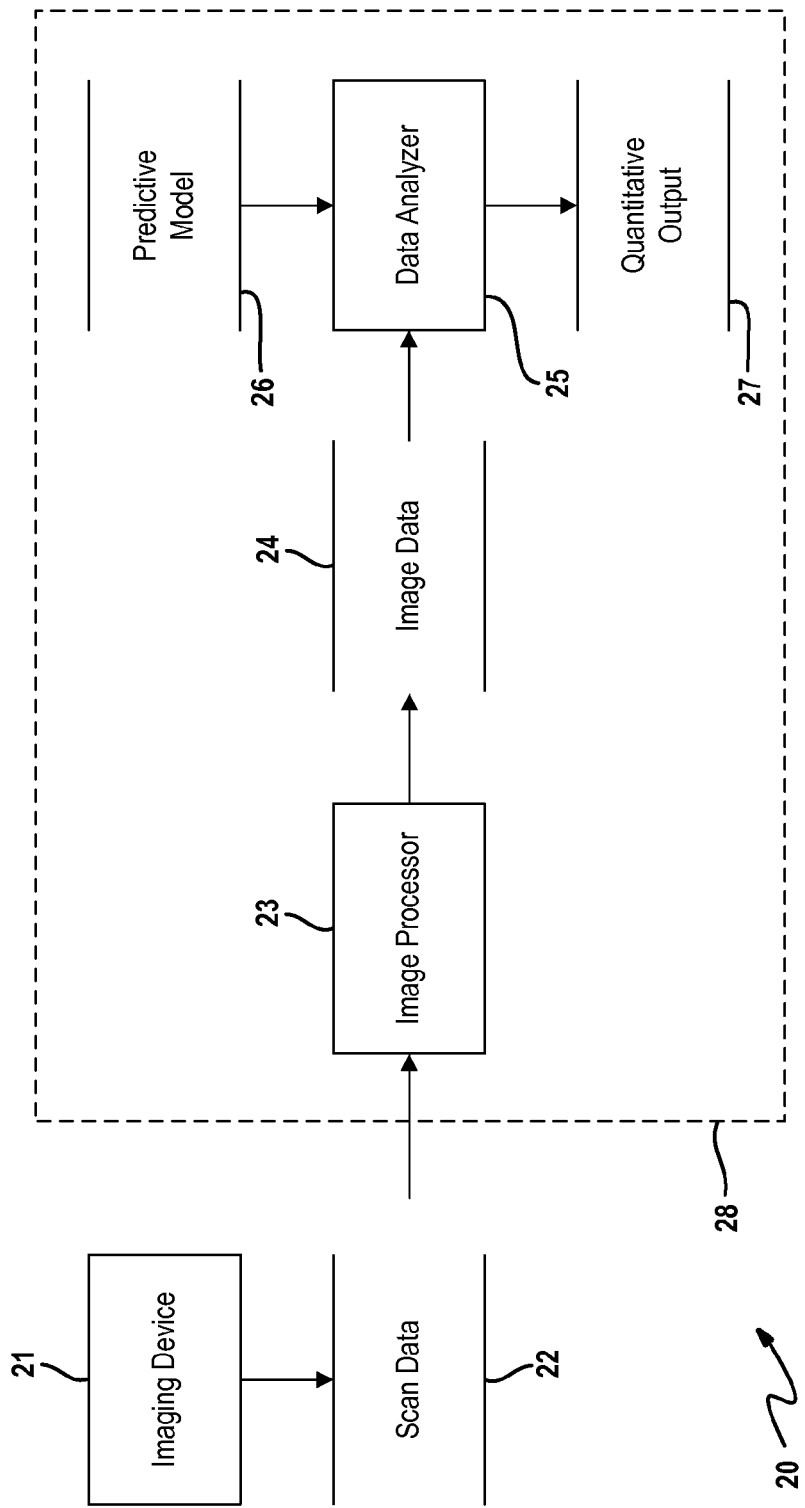
FIG. 2 is a diagram of an exemplary system for implementing the quantitative method set forth herein.

FIG. 2 depicts is a computer-implemented system 20 for detecting or diagnosing an undesirable medical condition of a liver in a subject. The system is comprised generally of an imaging device 21 and a computing device 28. The imaging device 21 is configured to capture scan data of the subject using, for example, computed tomography. Again, other types of imaging devices are contemplated by this disclosure.

On the other hand, the computing device 28 is comprised primarily of an image processor 23 and a data analyzer 25. The image processor 23 is configured to receive scan data 22 from the imaging device 21 and in turn extracts image data 24 representing the liver from the scan data. The data analyzer 25 is configured to evaluate the image data 24 in relation to a statistical model 26 predictive of a medical condition of a liver. The statistical model 26 resides in a data store of the computing device 28 and is comprised of at least one random variable, where the random variable is indicative of at least one of a shape or texture of the liver. The data analyzer 25 determines various measures of the liver from the image data 24 and then computes the random variables of the statistical model 26. In this way, the data analyzer 25 generates a quantitative output (e.g., probability) indicative of a medical condition of the liver from the statistical model.

Figure 3:
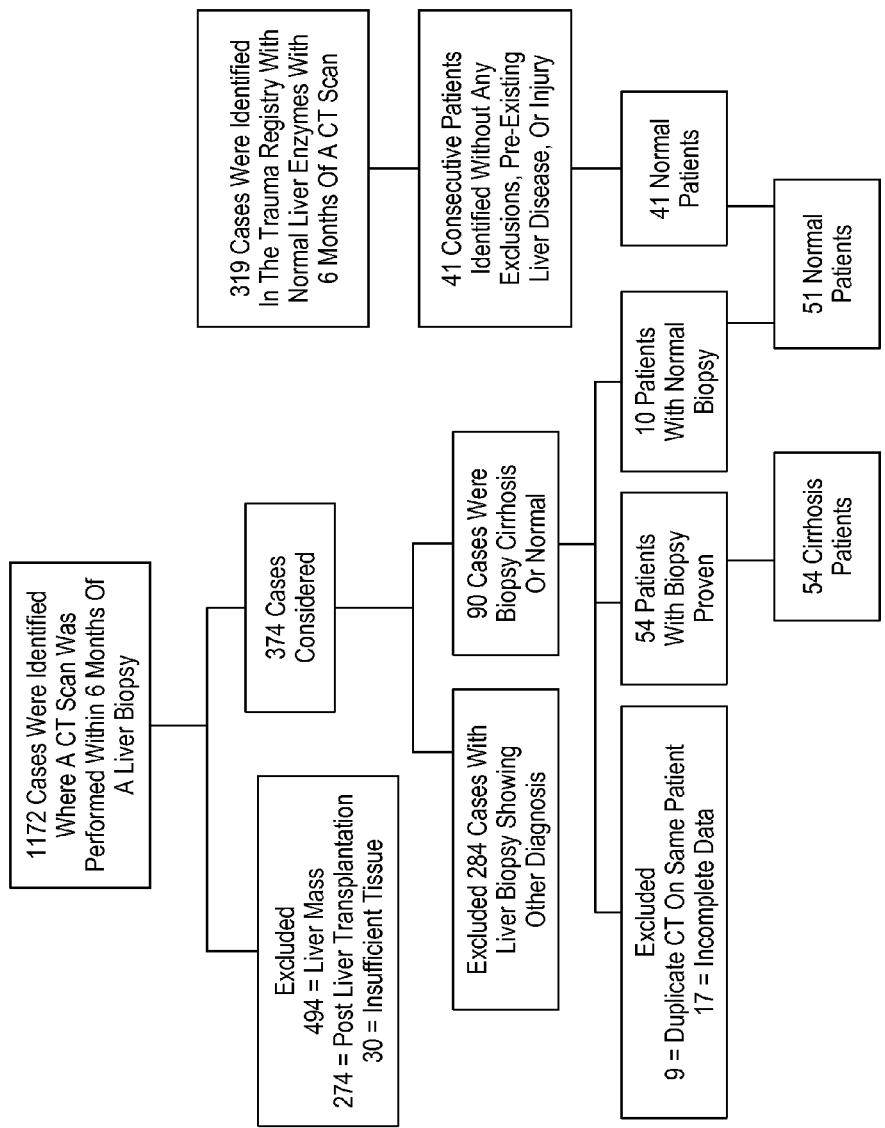
FIG. 3 is a diagram of data slice of a liver.

Further insights into this quantitative method and its development are further described below. Beginning with the selection of the patient population, the cohort of patients studied was identified through two mechanisms. The first was through the cross referencing of pathology and radiological clinical databases. All patients who had liver biopsies reviewed at the University of Michigan from January, 2004 to March of 2009 and a CT scan for any reason within 6 months of the liver biopsy were considered. All the clinical information for these patients were obtained from the electronic medical records and reviewed by two investigators. 1172 cases were found where a CT scan was performed within 6 months of a liver biopsy. Of these patients, 54 consecutive patients with cirrhosis and normal liver biopsy were identified as specified in FIG. 3. The second mechanism by which the patients were enrolled in this study was through the Trauma registry, where 41 consecutive patients were identified through the University of Michigan Trauma Registry from the period of March 2001 to August of 2009. Consecutive patients who had normal liver enzyme measurements (serum aminotransferase and alanine-aminotransferase) and a CT scan within 6 months of the laboratory tests were identified. All the patients' charts were reviewed to ensure that they had no evidence for liver disease by history, clinical or radiological exam. Patients meeting any of the following criteria were excluded from the study: liver mass, post liver transplantation, missing patient information such as height/weight, blood count or liver panel or insufficient liver tissue for patients who had liver biopsies. For each patient, only one CT scan per patient was utilized. In cases where multiple scans were found, the CT scan utilized was the scan which was closest in date to either the laboratory result (for the trauma patients) or closest to the liver biopsy.

In this study, the 105 livers were segmented from abdominal CT scans using Mimics software (Materialise, Leuven, Belgium) in a semi-automated fashion. The resulting external surface of each liver was saved as a stereo-lithography (STL) mesh into an Oracle database with Oracle Spatial data option (Oracle Corp., Redwood City, Calif.). Subsequently, each liver surface STL mesh, along with the DICOM (Digital Imaging and Communications in Medicine) files representing the CT scan was loaded into MATLAB® software (MathWorks Inc., Natick, Mass.). In MATLAB®, the STL mesh was used to limit the raw DICOM data to points within and on the liver surface. The result was a stack of CT slices where all the points outside the liver were excluded. This stack was then further restricted to the slice that included the left tip of the liver as well as two slices above and below that. This was done to create a subset of five slices that were easily defined and automatically collected. The resulting five CT slices per liver were then assessed using MATLAB® built-in routines as well as algorithms developed specifically for this study.

Figure 4:
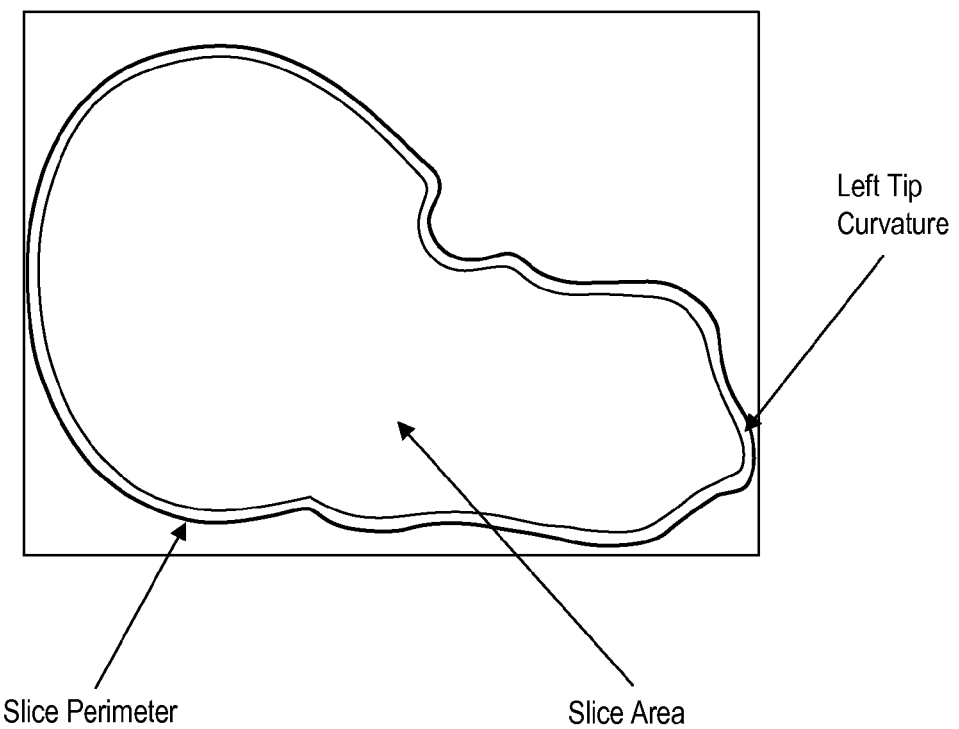
FIG. 4 is a diagram depicting patient selection criteria for the study described in this disclosure.

Multiple parameters were automatically calculated for each liver, represented by and averaged over the five CT slices. Ratios between the different measured parameters were also calculated, as well as ratios of the measured parameters to body surface area (BSA). Body surface area was calculated using the Dubois & Dubois formula: BSA $(m^2)=$ 0.007184*weight $(kg)^{0.425}$*height $(cm)^{0.725}$ although other computations for body surface area are contemplated by this disclosure. With regard to this study, all references to "slice" measurements represent the averages over the five representative slices as described above. Representation of the measurements of the slice parameters are illustrated in FIG. 4.

Liver slice-bounding box slice ratio calculation was based on the entropy function provided by MATLAB®, which defines entropy as:

$$-\sum_{l=1}^{k}([p(l)]*\log2[p(l)])$$

In the above formula, the summation is across all the gray levels l of the image. p(l) is the probability of the occurrence of the gray level l based on the image histogram technique. For the purposes of calculating this ratio using the entropy function, all the pixels outside the liver boundary were set to gray level value of 0. Thus, the liver slice-bounding box slice ratio signifies a value indicative of entropy of the slice data in relation to the bounding box.

Tortuosity was measured using two different methods. The first was based on a method in which the 3-dimensional tortuosity index ($TC_{3D}$) was defined in terms of 2-dimensional tortuosity indices in the X axis ($TC_X$) and Y axis ($TC_Y$) directions: $TC_{3D}=(TC_X^2+TC_Y^2)^{1/2}$. $TC_X$ and $TC_Y$ are defined as the sums of the absolute values of the differences between successive X coordinates and Y coordinates (15), respectively, divided by the sampling interval p, which in this research was set as the length of the slice perimeter of the slice with the left tip divided by 75. The second method for calculating tortuosity was the ratio of slice perimeter and slice area.

The left tip curvature was calculated utilizing the liver slice method and a custom MATLAB® routine. Curvature was defined as a reciprocal of radius, where radius in turn was solved as a least mean squares problem using a set of five points spaced evenly around the liver left tip, defining the left tip. Specifically, the set of five points chosen included the leftmost point of the liver, as well as the two points on either side of this point along the slice contour. The distance between each point was the sampling interval p, which was set as the length of the slice perimeter of the slice with the left tip divided by 75.

Liver volume and liver surface area were obtained directly from the Oracle database with built-in functions.

Liver slice perimeter and slice area were calculated using built-in MATLAB® routines. First, the stack of CT image slices for each liver was intersected with the corresponding 3-D liver surface contour created in Mimics, producing a new stack of slices consisting of image data within the liver boundary only. From this stack, the representative five slices were chosen. The average perimeter and the average area over these five slices were calculated for each liver.

The AST to Platelet Ratio Index (APRI) score was calculated as utilizing the formula: AST (IU/L)/Platelet count ($10^9$/L)×100, where an APRI<=1: cirrhosis unlikely, APRI>2: cirrhosis likely, and 1<APRI<=2: indeterminate. All laboratory values were within six months of the liver biopsy. If there was more than one set of laboratory values, the one temporally closest to the CT image was always utilized. In the analyses where the APRI-score was utilized, it was treated as a categorical variable with three categories.

Statistical analysis was performed using SAS software version 9.2 (SAS Institute Inc., Cary, N.C.). The endpoint of the study is the presence or absence of cirrhosis. Descriptive analyses were conducted on all measured and calculated variables. Both univariate and multivariate logistic regressions were performed to evaluate how these covariates are associated with biopsy-proven cirrhosis. Log transformation was utilized when the variables were non-normally distributed. Cirrhotic and normal patients were assigned randomly to the training or validation set in a 3:1 ratio. Only data from the training set was used to develop the predictive model, while the validation set was used to evaluate how the final model predicts the existence of cirrhosis for new samples. The variables in our final multivariate models were selected using backward selection, and also based on a priori knowledge of morphological changes that are known to occur with cirrhosis. The diagnostic ability of each predictive model was assessed by the area under the receiver operating characteristic curves (AUROC). Each model derived from the training set was then applied to the livers in the validation set to test the model for accuracy by measuring the AUROC. All p-values were calculated along with two-sided tests. A p value of less than 0.05 was considered statistically significant. All data is expressed as mean±SEM unless otherwise noted.

During the period of January 2004 to March of 2009, 4165 liver biopsies were found in the University of Michigan pathology database. This database was cross-referenced with the University of Michigan radiology database to identify patients who had a CT scan for any reason within 6 months of the liver biopsy. 64 patients were identified in this fashion, 10 of whom had normal liver biopsies and 54 of whom had cirrhosis on liver biopsy. Of the patients with cirrhosis: 15 had hepatitis C, 13 had cryptogenic cirrhosis, 7 had nonalcoholic fatty liver disease, 6 had alcoholic liver disease, 5 had autoimmune hepatitis, 2 had autoimmune cholangiopathy, 4 had primary sclerosing cholangitis, 1 had alpha-1-antitrypsin deficiency and 1 had hepatitis B. Because the number of patients with normal liver biopsy who had also had a CT scan within 6 months of the liver biopsy was very small, additional normal patients were identified through the Trauma registry. Patients were randomly divided into a training set (n=81) and a validation set (n=24). As noted in Table 1 below, the patient characteristics including age, gender, and body surface area were not significantly different between the two groups. Similarly, the proportions of patients with cirrhosis and with different APRI scores or designations were also not significantly different between the training and validation sets.

TABLE I

Patient Characteristics

| | Training set (n = 81) | Validation set (n = 24) | p Value |
|---|---|---|---|
| Diagnosis | | | 0.87 |
| Cirrhosis (%) | 42 (52) | 12 (50) | |
| Normal (%) | 39 (48) | 12 (50) | |
| Age, years | 41.83 ± 2.17 | 42.5 ± 4.12 | 0.90 |
| Male gender, n (%) | 39 (48) | 10 (42) | 0.58 |
| Body surface area, m² | 1.91 ± 0.036 | 1.84 ± 0.052 | 0.39 |
| Child's Classification (of cirrhotic livers) | | | 0.97 |
| A (%) | 21 (50) | 6 (50) | |
| B (%) | 15 (36) | 4 (33) | |
| C (%) | 6 (14) | 2 (17) | |
| Cirrhosis with ascites (%) | 18 (43) | 6 (50) | 0.78 |
| Cirrhosis with encephalopathy, n (%) | 6 (14) | 0 (0) | 0.17 |
| MELD | 12.24 ± 0.78 | 12.08 ± 1.07 | 0.94 |
| APRI | 1.54 ± 0.29 | 1.23 ± 0.34 | 0.59 |

TABLE I-continued

Patient Characteristics

| | Training set (n = 81) | Validation set (n = 24) | p Value |
|---|---|---|---|
| APRI CLASSIFICATION | | | 0.20 |
| Cirrhosis likely (%) | 14 (17) | 6 (25) | |
| Cirrhosis, unlikely (%) | 47 (58) | 16 (67) | |
| Indeterminate (%) | 20 (25) | | |

In order to identify morphologic features which could predict cirrhosis, various parameters were considered. As expected, there was no statistically significant difference in any of the measured characteristics of the CT scans between the training and validation set (Table 2). Of note, 79 of the 105 scans were performed with intravenous contrast and 26 were not. Only 4 of the scans were triple phase scans (noncontrast, arterial and portal venous phases) and in these cases only one phase was randomly used. No specific CT scan density data based on Hounsfield units were utilized.

TABLE II

CT characteristics.

| Measured Parameter | Training set (n = 81) | Validation set (n = 24) | p Value |
|---|---|---|---|
| Liver slice-bounding box slice ratio | 1.13 ± 0.018 | 1.15 ± 0.041 | 0.59 |
| Tortuosity | 13.64 ± 0.19 | 13.65 ± 0.32 | 0.97 |
| Left tip curvature | 0.054 ± 0.0022 | 0.059 ± 0.0041 | 0.27 |
| Liver volume, mm$^3$ | 1706455.04 ± 67862.31 | 1628709.27 ± 108097.18 | 0.57 |
| Liver area, mm$^2$ | 90991.84 ± 2403.91 | 87922.42 ± 3897.34 | 0.53 |
| Slice perimeter, mm | 854.40 ± 14.83 | 837.64 ± 31.10 | 0.60 |
| Slice area, mm$^2$ | 35243.56 ± 991.40 | 34068.64 ± 2015.66 | 0.58 |
| Bounding box X-dim, mm | 208.94 ± 3.27 | 205.22 ± 5.87 | 0.58 |
| Bounding box Y-dim, mm | 178.22 ± 3.12 | 167.60 ± 4.95 | 0.10 |
| Bounding box Z-dim, mm | 164.24 ± 3.24 | 160.29 ± 5.95 | 0.56 |
| Bounding box volume, mm$^3$ | 6259639.10 ± 246231.20 | 5661354.42 ± 436986.98 | 0.24 |

Univariate analysis was performed to identify differences between cirrhotic and normal cases in regards to patient characteristics (Table 3A) and CT characteristics (Table 3B and 3C). The variables shown in Tables 3A, 3B, and 3C with p-values <0.05 were identified to be significantly different between cirrhotic and normal livers. On multivariate analysis, the only variables which remained significant were liver slice—bounding box slice ratio (p=0.03), APRI classification (p=0.03), and bounding box Z dimension divided by liver area (p=0.03).

TABLE III

Univariate analysis within the training set (n = 81).

| Parameter | Cirrhosis | Normal | p Value |
|---|---|---|---|
| A. Patient characteristics | | | |
| N | 42 | 39 | |
| Age, years | 51.26 ± 2.24 | 31.67 ± 3.08 | <0.01 |
| Male gender, n (%) | 24 (57) | 16 (41) | 0.15 |
| APRI | 2.28 ± 0.47 | 0.63 ± 0.22 | <0.01 |
| APRI CLASSIFICATION | 12 (29) | 2 (5) | <0.01 |
| Cirrhosis likely (%) | | | |
| Cirrhosis unlikely (%) | 17 (40) | 30 (77) | |
| Cirrhosis indeterminant (%) | 13 (31) | 7 (18) | |
| BSA, m$^2$ | 1.95 ± 0.050 | 1.87 ± 0.052 | 0.27 |
| B. CT characteristics: measured parameters | | | |
| Liver slice-bounding box slice ratio | 1.06 ± 0.020 | 1.21 ± 0.027 | <0.01 |
| Tortuosity | 13.30 ± 0.31 | 14.01 ± 0.21 | 0.066 |
| Left tip curvature | 0.053 ± 0.0031 | 0.055 ± 0.0033 | 0.57 |
| Liver volume, mm$^3$ | 1808007.64 ± 116806.3 | 1597090.71 ± 60632.23 | 0.12 |
| Liver area, mm$^2$ | 94122.19 ± 4123.06 | 87620.70 ± 2222.18 | 0.18 |
| Slice perimeter, mm | 851.44 ± 23.03 | 857.59 ± 18.56 | 0.84 |
| Slice area, mm$^2$ | 34256.02 ± 1522.00 | 36307.07 ± 1244.38 | 0.30 |
| Bounding box X-dim*, mm | 218.38 ± 5.21 | 198.78 ± 3.15 | <0.01 |
| Bounding box Y-dim, mm | 187.74 ± 4.58 | 167.98 ± 3.56 | <0.01 |
| Bounding box Z-dim, mm | 160.41 ± 5.50 | 168.36 ± 3.14 | 0.22 |
| Bounding box volume, mm$^3$ | 6809806.33 ± 415184.53 | 5667151.31 ± 216776.97 | 0.019 |

TABLE III-continued

Univariate analysis within the training set (n = 81).

| Parameter | Cirrhosis | Normal | p Value |
|---|---|---|---|
| C. CT characteristics: calculated parameters | | | |
| Liver volume/bounding box volume | 0.27 ± 0.0060 | 0.28 ± 0.0038 | 0.029 |
| Liver volume/BSA, mm$^3$/mm$^2$ | 922007.17 ± 53882.57 | 859738.81 ± 24993.26 | 0.31 |
| Liver area/BSA, mm$^2$, m2 | 48451.93 ± 1805.25 | 47657.28 ± 1171.03 | 0.71 |
| ln (liver area/BSA) | 10.76 ± 0.037 | 10.76 ± 0.025 | 0.995 |
| Slice perimeter/BSA, mm/m$^2$ | 452.02 ± 19.34 | 476.38 ± 18.40 | 0.37 |
| ln (slice perimeter/BSA) | 6.08 ± 0.039 | 6.14 ± 0.040 | 0.32 |
| Slice perimeter/slice area, 1/mm | 0.026 ± 0.00063 | 0.024 ± 0.00045 | 0.034 |
| Slice area/BSA, mm$^2$/m$^2$ | 18166.30 ± 1010.31 | 20070.24 ± 882.99 | 0.16 |
| Liver bounding box X-dim/Y-dim | 1.18 ± 0.036 | 1.20 ± 0.030 | 0.71 |
| Liver bounding box X-dim/Z-dim | 1.42 ± 0.056 | 1.19 ± 0.024 | <0.01 |
| Liver bounding box Y-dim/Z-dim | 1.20 ± 0.033 | 1.01 ± 0.025 | <0.01 |
| Bounding box X-dim/liver area, 1/mm | 0.0025 ± 0.000088 | 0.0023 ± 0.000047 | 0.15 |
| Bounding box Y-dim/liver area, 1/mm | 0.0021 ± 0.000061 | 0.0019 ± 0.000041 | 0.050 |
| Bounding box Z-dim/liver area, 1/mm | 0.0018 ± 0.000050 | 0.0019 ± 0.000037 | <0.01 |

To achieve diagnostic ability using the measured variables and account for the confounding effects within the covariates, multiple logistic regression models were fit to identify a set of predictors for cirrhosis. Specifically, see the following model $$\log\left(\frac{p_i}{1-p_i}\right) = \text{Intercept} + \alpha_1 * \text{variable } 1_i + \ldots + \alpha_k * \text{variable } k_1,$$

where $p_i$ is the probability of developing cirrhosis for subject i, $\alpha_1, \alpha_2 \ldots$ are the coefficients to estimate, and k is the number of variables in the logistic regression model. For any given set of parameters, $$\log\left(\frac{p_i}{1-p_i}\right),$$

commonly referred to as the LOGIT of $p_i$, can be calculated, and therefore an estimate of $p_i$ can be obtained for each subject. In Table 4 below, five promising models are presented utilizing 2 to 7 variables.

TABLE IV

Best candidate models.

| | Training set | | Validation set |
|---|---|---|---|
| Parameters in the Model | x$^2$ Score | Prediction of cirrhosis AUC | Prediction of Cirrhosis AUC |
| 2 Variables in the model: | | | |
| Liver slice-bounding box slide ratio, liver bbox* Y-dim$^1$/X-dim | 27.54 | 0.82 | 0.86 |
| 3 Variables in the model: | | | |
| Liver slice-bounding box slice ratio, liver bbox Y-dim/Z-dim, liver volume/bbox volume | 24.88 | 0.82 | 0.85 |
| Liver slice-bounding box slice ratio, liver bbox Y-dim/Z-dim | 24.17 | 0.82 | 0.86 |
| 4 Variables in the model: | | | |
| Liver slice-bounding box slice ratio, liver volume/bbox volume, liver bbox X-dim/Z-dim, liver bbox Y-dim/Z-dim | 25.88 | 0.83 | 0.85 |
| 5 Variables in the model: | | | |
| Liver slice-bounding box slice ratio, slice perimeter/slice area, liver volume/bbox volume, bbox Y-dim/liver area, bbox Z-dim/liver area | 26.87 | 0.84 | 0.84 |

TABLE IV-continued

Best candidate models.

| Parameters in the Model | $x^2$ Score | Training set Prediction of cirrhosis AUC | Validation set Prediction of Cirrhosis AUC |
|---|---|---|---|
| 7 Variables in the model: | | | |
| Liver slice-bounding box slice ratio, ln(slice perimeter/BSA), slice area/BSA, liver volume/BSA, ln (liver area/BSA), liver bbox X-dim/Y-dim, liver bbox X-dim/Z-dim | 12.44 | 0.70 | N/A |
| 7 Variable + APRI in the model: | | | |
| APRI score, liver slice-bounding box slide ratio, ln (slice perimeter/BSA), slice area/BSA, liver volume/BSA, ln(liver area/BSA), liver bbox X-dim/Y-dim, liver bbox X-dim/Z-dim | 48.00 | 0.95 | N/A |

*Bounding box.
†Dimension

The most promising model is defined as the one which obtains the highest chi-square score when fixing the number of variables in the model. AUROC was calculated under each developed model for both training set and validation set. All these predictive models, when applied to the validation set, yielded an AUROC of at least 0.85. The 7-variable model achieved the highest AUROC for the training and validation sets, 0.90 and 0.91 respectively. By comparison, utilization of the APRI-score to predict cirrhosis in our training dataset yielded only an AUROC of 0.70. In examining the utility of the APRI score, the APRI score alone predicted that 'cirrhosis unlikely' for 40% of patients with biopsy proven cirrhosis. In addition, the APRI score incorrectly identified 5% of the normal patients as 'cirrhosis likely'. In the validation set, there were two cirrhotic cases for which the APRI classification was 'indeterminate' where the patients were known to have biopsy proven cirrhosis. In contrast to the APRI score, each of the 6 models presented in Table 4 correctly diagnosed these two cases as cirrhotic. To determine if the addition of APRI to our model would be helpful, the AUROC for a model which included both the APRI-score and 7-variable model was calculated, and found an improved AUROC of 0.95.

This disclosure has demonstrated that one can quantitatively measure the morphological features of cirrhosis by computationally processing the DICOM files of CT scans in a three dimensional spatially oriented database. With this technique, models were created to predict cirrhosis based on CT imaging. Morphological features such as contour and dimensions were very predictive of cirrhosis.

One exemplary predictor for cirrhosis is dimensional changes in the liver. With development of cirrhosis there is variable hypertrophy and atrophy of different aspects of the liver segments. By measuring multiple dimensional ratios, changes in the X, Y, Z dimensions of the bounding box were predictive of cirrhosis. For example, one parameter which was significant on univariate analysis was the liver bounding box Y-dimension and Z-dimension ratio. Using just this parameter and the liver slice—bounding box slice ratio we were able to create a 2 variable model which achieved an AUROC of 0.86 for the validation set. As shown in Table 3B, this ratio was higher in cirrhotic livers consistent with more hypertrophy in the antero-posterior dimension than the craniocaudal dimension. Other morphological changes which have been reported in cirrhotic livers include caudate lobe hypertrophy and segmental hypertrophy in the lateral segments (II, III) of the left lobe, as well as segmental atrophy of both the posterior segments (VI, VII) of the right lobe and medial segment (IV) of the left lobe. These changes in the shape of the liver can be measured by changes in the bounding box ratios. While calculation of liver volume is a common practice and is useful for planning liver surgery, this calculation by itself was not sufficient to predict cirrhosis in our study or others. Rather, it is the parameters derived from liver volume which reached statistical significance (Table 3C), such as liver volume—bounding box volume ratio, as well as the ratios of the dimensions of the bounding box itself. These measurements are more reflective of contour and shape.

Because the scans utilized were not protocol specific and were conducted both with and without intravenous contrast, it was determined not to measure changes in attenuation within the liver. Previously, Romero-Gomez described a technique of measuring differential optical density in non-contrasted CT scans to evaluate fibrosis in patients with hepatitis C. One disadvantage in this approach was that studies had to be protocol dependent. Furthermore, the accuracy of the technique was highly dependent on the homogenous nature of the fibrosis with significant decline in accuracy when the disease was heterogeneous. Thus, it is not clear if the technique could be broadly applied to diseases other than hepatitis C. In this study, a heterogeneous population of patients with a wide range of liver diagnoses was utilized. CT scans used in the study were performed with a wide variety of protocols. Less dependence on strict protocol application will allow for broader use and allows the technique to be used on "incidental" scans, thus decreasing costs and radiation exposure.

In this study, the APRI score was not very helpful in determining cirrhosis with an AUROC of only 0.70. This is not surprising since the APRI score has been found to be useful in hepatitis C patients and is not necessarily applicable to different types of liver disease. Nevertheless, the addition of the APRI score to the predictive models significantly increased the AUROC suggesting that multi-modal approaches may be most helpful.

This study shows proof of concept that quantitative image analysis of livers on CT scans, based on analysis of morphological features, may be utilized to predict cirrhosis in the absence of a liver biopsy. While other noninvasive measures of fibrosis and cirrhosis have been proposed, the key differentiator in this approach is that this is an automated analysis framework which is not based on assessments by individual observers. Furthermore, there is no requirement for specialized laboratory assessments, specialized equipment, or specialized protocols, not commonly available in a community hospital. The analysis of the data requires only uploading of the DICOM data file from any CT scan and can even occur through web based portals. Furthermore, it was shown that the addition of simple serum based studies such as APRI can yield even higher accuracies.

Lastly, techniques presented in this disclosure can be extended to other areas. An area of particular interest to is predicting risk of death and complications from surgical procedures. In this scenario, patients often already have had a CT scan for their clinical problems such as aortic aneurysms. In this setting, the "incidental" CT scan can be further analyzed for assess surgical risk in conjunction with other predictors. Another scenario for which this technology may be useful is in the patient with thrombocytopenia where the undiagnosed cirrhosis is part of the differential diagnosis. In this scenario, patients often already had a CT scan to rule out other liver diseases and causes of thrombocytopenia. Quantitative analysis of such CT scans could provide important clinical information to assess the risk and benefit of a liver biopsy. In addition to CT scans, the techniques described here can be modified to analyze MRI scans. This approach has many potential clinical implications and may be another tool in the search for noninvasive assessments of liver disease.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for detecting an undesirable medical condition of a liver in a subject, comprising:
    capturing scan data of the subject using computed tomography, where the scan data includes the liver of the subject;
    constructing a three-dimensional surface model of a liver from the scan data;
    extracting image data representing the liver from the scan data using the three-dimensional surface model, where the image data is comprised of a stack of two-dimensional data slices;
    determining a measure of the liver from the image data;
    determining a random variable from the measure of the liver, where the random variable is indicative of at least one of a shape or texture of the liver; and
    detecting an undesirable condition of the liver using a statistical model comprised of the random variable.

2. The computer-implemented method of claim 1 further comprises identifying a given data slice from the stack of data slices; and determining the measure of the liver from the given data slice.

3. The computer-implemented method of claim 2 further comprises identifying the given data slice as having a left tip of the liver.

4. The computer-implemented method of claim 2 wherein determining a random variable includes computing a perimeter of the given data slice, computing an area for the given data slice and determining a ratio between the perimeter and the area of the given data slice.

5. The computer-implemented method of claim 2 wherein determining a random variable includes computing a perimeter of the given data slice, computing an area for the given data slice, and determining a ratio between a body surface area for the subject and either the perimeter or the area of the given data slice.

6. The computer-implemented method of claim 5 wherein determining a random variable includes computing a ratio between a body surface area for the subject and either a volume or surface area of the liver.

7. The computer-implemented method of claim 2 wherein determining a random variable includes constructing a bounding box which encases the liver and computing a value indicative of entropy of the given data slice in relation to the bounding box.

8. The computer-implemented method of claim 1 wherein the determining a measure of the liver includes computing at least one of a volume or surface area of the liver.

9. The computer-implemented method of claim 1 further comprises determining a probability of the undesirable condition of the liver using a logistic regression model.

10. A computer-implemented method for detecting an undesirable medical condition of a liver in a subject, comprising:
receiving image data representing a liver of a subject;
determining a measure of the liver from the image data by constructing a bounding box which encases the liver and calculating at least one dimension of the bounding box;
determining a random variable from the measure of the liver, where the random variable is indicative of at least one of a shape or texture of the liver; and
detecting an undesirable condition of the liver using a statistical model comprised of the random variable.

11. The computer-implemented method of claim 10 wherein determining a random variable includes computing a ratio between two dimensions of the bounding box.

12. The computer-implemented method of claim 10 wherein determining a random variable includes computing a volume of the liver from the image data and computing a ratio between the volume of the liver and a volume of the bounding box.

13. A computer-implemented method for detecting an undesirable medical condition of a liver in a subject, comprising:
constructing a statistical model predictive of a medical condition of a liver, the statistical model comprised of at least one random variable that is indicative of at least one of a shape or texture of the liver;
capturing scan data of the subject using computed tomography, where the scan data includes the liver of the subject;
extracting the image data representing the liver from the scan data, where the image data is comprised of a stack of two-dimensional data slices;
identifying a given data slice from the stack of data slices, where the given data slice includes a left tip of the liver;
determining a measure of the liver from the given data slice;
determining the random variable from the measure of the liver; and
determining a probability of the medical condition of the liver from the statistical model.

14. A computer-implemented system for detecting an undesirable medical condition of a liver in a subject, comprising:
an image processor configured to receive image data for a subject and operable to extract a subset of the image data, where the subset of image data includes the liver of the subjects;
a statistical model predictive of a medical condition of a liver, the statistical model comprised of at least one random variable and the random variable is indicative of at least one of a shape or texture of the liver; and
a data analyzer configured to receive the subset of image data as a stack of two-dimensional data slices and operates to identify a given data slice from the stack of data slices and determine measure of the liver from the given data slice, the data analyzer further operable to compute the random variable from the measure of the liver and determine the medical condition of the liver from the statistical model, wherein the image processor and the data analyzer are implemented as computer executable instructions executed by a computer processor.

15. The computer-implemented system of claim 14 further comprises an imaging device configured to capture the image data for the subject using computed tomography.

16. The computer-implemented system of claim 14 wherein the data analyzer further operates to construct a bounding box which encases the liver, determine at least one dimension of the bounding box and determine a measure of entropy of the given data slice in relation to the bounding box.

17. The computer-implemented system of claim 16 wherein statistical model includes a first random variable defined as the entropy measure and a second random variable defined as a ratio between two dimension of the bounding box and the entropy measure.

18. The computer-implemented system of claim 17 wherein statistical model includes a third random variable defined as a ratio between a volume of the liver and a volume of the bounding box.

19. The computer-implemented system of claim 18 wherein statistical model includes a fourth random variable defined as a ratio between a perimeter of the given data slice and an area of the given data slice.

20. The computer-implemented system of claim 17 wherein statistical model includes a third random variable defined a ratio between a perimeter of the given data slice and a body surface area for the subject, fourth random variable defined as a ratio between an area of the given data slice and the body surface area for the subject, a fifth random variable defined as a ratio between a volume of the liver and the body surface area for the subject, and a sixth random variable defined as a ratio between a surface area of the liver and the body surface area for the subject.

21. The computer-implemented system of claim 17 wherein statistical model includes a seventh random variable defines as aspartate transaminase to platelet ratio index (APRI) score.

22. The computer-implemented system of claim 14 wherein statistical model is further defines as a logistic regression model.

* * * * *